(12) United States Patent
Neumann et al.

(10) Patent No.: US 9,107,981 B2
(45) Date of Patent: Aug. 18, 2015

(54) ANTIBACTERIAL COATING FOR AN IMPLANT AND METHOD FOR PRODUCING SAID COATING

(75) Inventors: Hans-Georg Neumann, Rostock (DE); Cornelia Prinz, Marlow (DE); Ulrich Lembke, Rostock (DE)

(73) Assignee: DOT GMBH, Rostock (DE)

( * ) Notice: Subject to any disclaimer, the term of this patent is extended or adjusted under 35 U.S.C. 154(b) by 0 days.

(21) Appl. No.: 13/989,650

(22) PCT Filed: Nov. 28, 2011

(86) PCT No.: PCT/EP2011/005963
§ 371 (c)(1),
(2), (4) Date: May 24, 2013

(87) PCT Pub. No.: WO2012/076124
PCT Pub. Date: Jun. 14, 2012

(65) Prior Publication Data
US 2013/0252021 A1    Sep. 26, 2013

(30) Foreign Application Priority Data

Dec. 10, 2010    (DE) .......................... 10 2010 054 046

(51) Int. Cl.
*B32B 9/00*       (2006.01)
*A61L 27/30*      (2006.01)
*A61L 27/06*      (2006.01)
*A61L 27/54*      (2006.01)
*C09D 5/14*       (2006.01)

(52) U.S. Cl.
CPC .............. *A61L 27/306* (2013.01); *A61L 27/06* (2013.01); *A61L 27/54* (2013.01); *C09D 5/14* (2013.01); *A61L 2300/102* (2013.01); *A61L 2300/404* (2013.01); *A61L 2300/608* (2013.01); *Y10T 428/12785* (2015.01); *Y10T 428/265* (2015.01); *Y10T 428/31678* (2015.04)

(58) Field of Classification Search
None
See application file for complete search history.

(56) References Cited

U.S. PATENT DOCUMENTS

| | | | | |
|---|---|---|---|---|
| 4,745,035 | A | * | 5/1988 | Saurer et al. .................. 428/614 |
| 5,958,440 | A | * | 9/1999 | Burrell et al. ................. 424/409 |
| 6,113,636 | A | * | 9/2000 | Ogle ........................... 623/11.11 |
| 6,267,782 | B1 | * | 7/2001 | Ogle et al. ...................... 623/1.1 |
| 7,211,323 | B2 | * | 5/2007 | Erdemir et .................... 428/323 |

(Continued)

FOREIGN PATENT DOCUMENTS

| | | | | |
|---|---|---|---|---|
| CN | 101705468 | * | 5/2010 | ............ A01N 59/16 |
| DE | 601 21 315 T2 | | 7/2007 | |

(Continued)

OTHER PUBLICATIONS

Myung et al., "A study on the synthesis and formation behavior of nanostructured TiN films by copper doping", 2004, Surface and Coatings Technology, 177-178, pp. 404-408.*

(Continued)

*Primary Examiner* — Humera Sheikh
*Assistant Examiner* — Seth Dumbris
(74) *Attorney, Agent, or Firm* — McNees Wallace & Nurick LLC

(57) ABSTRACT

An antibacterial coating for an implant is provided that contains copper. A method of producing an antibacterial coating for an implant is also provided that includes the coating being applied by a PVD process and the layer generated by the PVD process includes a copper content.

12 Claims, 1 Drawing Sheet

(56) References Cited

U.S. PATENT DOCUMENTS

| | | | |
|---|---|---|---|
| 8,530,056 B2* | 9/2013 | Pilloy et al. | 428/432 |
| 2001/0055622 A1 | 12/2001 | Burrell et al. | |
| 2002/0168552 A1* | 11/2002 | Yamamoto et al. | 428/697 |
| 2006/0161256 A1* | 7/2006 | Ziegler et al. | 623/11.11 |
| 2009/0082866 A1* | 3/2009 | Link et al. | 623/16.11 |
| 2009/0162695 A1* | 6/2009 | Hevesi et al. | 428/698 |
| 2009/0198343 A1 | 8/2009 | Spain et al. | |
| 2012/0059278 A1* | 3/2012 | Bissell | 600/570 |

FOREIGN PATENT DOCUMENTS

| | | |
|---|---|---|
| EP | 1632198 A1 | 3/2006 |
| WO | 2009/111307 A2 | 9/2009 |
| WO | 2010/106164 A1 | 9/2010 |

OTHER PUBLICATIONS

Tian et al., "Antibacterial copper-containing titanium nitride films produced by dual magnetron sputtering", 2007, Surface and Coatings Technology, 201, pp. 8606-8609.*

Kelly et al., "Comparison of the tribological and antimicrobial properties of CrN/Ag, ZrN/Ag, TiN/Ag, and TiN/Cu nanocomposite coatings", 2010, Surface and Coatings Technology, 205, pp. 1606-1610.*

Ewald Andrea et al., "Antimicrobial titanium/silver PVD coatings on titanium", Biomedical Engineering Online, Biomed Central Ltd, Bd. 5, Nr. 1, 24, Mar. 24, 2006.

Heidenau F. et al., "A novel antibacterial titania coating: Metal ion toxicity and in vitro surface colonization", Journal of Materials Science: Materials in Medicine, Kluwer Academic Publishers, BO, Bd. 16, Nr. 10, Oct. 1, 2005.

Warner, G.B., "The Role of Antimicrobial Silver Nanotechnology", MDDI, Aug. 2005, http://www.devicelink.com/mddi/archive/05/08/005.html.

Kataloq des Institutes fur Laboratoriumdiagnostik, May 2005, 41 pgs, no english translation available.

* cited by examiner

ANTIBACTERIAL COATING FOR AN IMPLANT AND METHOD FOR PRODUCING SAID COATING

BACKGROUND OF THE INVENTION

The present invention relates to an antibacterial coating for an implant and to a method of producing this coating.

It is generally known that silver has a high antibacterial activity. It is also already described in the prior art to use silver in a coating for implants. Examples are found in WO 2010/106164 A1 and in EP 1 632 198 B1. Such a coating offers advantages if the implant comes into contact with bacteria during the surgery or in the surgery wound, for example if bacteria reach the wound in an undesirable manner during the surgery or if bacteria are already present in the wound due to an existing infection.

But it is also known from the literature that silver ions also have a cytotoxic effect. This effect starts even with concentrations of above 380 µg/l (see, for example, Heidenau, F., Mittelmeier W., Detsch R., Haenle M., Stenzel F., Zeigler G., Gollwitzer H., 2005: "A novel antibacterial titania coating: Metal ion toxicity and in vitro surface colonization", J. Materials Science, Materials in Medicine 16, 1-6").

The cytotoxicity of silver ions that has been observed even with such low concentrations corresponds to the fact that silver does not play a role in the metabolism of the cell; silver is not part of the so-called essential trace elements in the human organism. The intake of low doses of silver, as well as a release from silver surfaces occurring over a longer period of time may lead to permanent cell damage. The WHO recommends that the consumption of silver should not exceed 180 µg per day (see, for example, Gibbins, B., Warner, L., 2005: "The Role of Antimicrobial Silver Nanotechnology", MDDI, http://www.devicelink.com/mddi/archive/05/08/005.html, 05.02.08).

It is also known that copper has an antibacterial activity, which, however, is lower than the antibacterial activity of silver. In contrast to silver, copper ions, in moderate concentrations, do not cause cell damage (see the above-mentioned publication of Heidenau et al.); they are, however, of essential importance to the metabolism of the cells and are present in the body media at concentrations of from 11 to 24 µmol/l (see, for example, catalog of the Inst. f. Labordiagnostik Klinikum Süd, Rostock, Germany, 2005).

Accordingly, antibacterial coatings that use copper have also already been described in the prior art. One example is found in U.S. Pat. No. 5,958,440, in which an antibacterial coating with copper, among others, is applied by means of a PVD (physical vapor deposition) process. In that document, however, only layers having a limited hardness are obtained, which are not suitable for a number of applications.

The object of the invention is to propose surface layers which combine the existing advantages of the PVD layers, such as good adhesion and high hardness, with an antibacterial activity of the layer, and also a method for an effective production of such surface layers.

BRIEF SUMMARY OF THE INVENTION

To achieve this object, according to the invention provision is made for an antibacterial coating for an implant, the coating being characterized in that it contains copper. The invention is based on the finding that an antibacterial activity can be obtained by adding copper to the coating, without the mechanical properties of the coating being substantially affected thereby, in particular the hardness, and without this resulting in an increase in manufacturing expenditure. It is taken into consideration here that even comparatively small amounts of copper have a sufficient antibacterial activity, although copper as such has a lower antibacterial activity than silver. The cytotoxic effect of silver, on the other hand, starts at markedly lower concentrations than in the case of copper.

The antibacterial activity allows the activity of bacteria which reach the implant or are transported into the wound in an undesirable manner during the insertion of the implant into the body, or are already present in the body due to an infection, to be considerably reduced. If the activity of any bacteria that may be present is reduced, the newly forming bone tissue is able to better connect to the implant. In addition, the amount of medication against infections that needs to be administered after the surgery may be lowered, which has a positive overall effect on the healing process after the implantation.

The term "implant" in this connection is meant to include any component part that is intended to remain within the body of a human being or an animal over a longer period of time, e.g. in the form of a bone nail, part of an artificial joint, bone substitute, artificial organ, etc.

Preferably, provision is made that besides copper, the coating contains at least one of the following components: Ti, Zr, Nb, Ta, Cr, Mo, W, Si, Al. These components allow a very high hardness of the coating to be achieved, even in the presence of copper. The biocompatible components Ta, Ti and Nb are especially preferred.

At least one metallic component may be bound in the form of nitrides, carbides or oxides. Nitrides and carbides have the advantage of a particularly high hardness. Oxides offer advantages with respect to their surface structure. In this way, layers having different tribological properties and different temperature resistances may also be produced. The possibility of producing layers having favorable tribological properties is of great importance, specifically for implants.

In the case of multilayer layers, an alternation between pure metal layers and layers with nitrides, oxides and carbides is possible here; each individual layer may or may not contain copper but, according to the invention, contains at least one layer of copper such that copper ions can be released and the release is not completely prevented by overlying layers, but is at most retarded to a desired extent.

According to a preferred embodiment of the invention, provision is made that the coating contains at least one layer of copper titanium nitride. This embodiment takes up the titanium nitride coatings which are already known and well-proven and which are used in particular for implants. According to the invention, the additional proportion of copper allows an antibacterial activity to be achieved without the other properties and the resultant advantages of this coating being affected.

The selectable proportion of copper in the layer according to the invention is a function of the desired maximum copper concentration in the body fluid surrounding the implant, the rate at which copper is catabolized in the respective surroundings, the rate of release of copper from the layer according to the invention, and the period of time in which a release of copper is to occur. Here, a concentration of 200 µmol/l should not be exceeded since the copper has a cytotoxic effect at concentrations higher than this.

Preferably, provision is made that the coating can release copper at a rate such that a copper concentration of from 90 to 160 µmol/l is obtained in a test fluid which surrounds the implant and physiologically corresponds to a body fluid in a wound of the body. Since even a considerably lower proportion of copper in the surrounding body fluid has a sufficient antibacterial activity, the coating according to the invention may be designed such that it falls considerably short of the above-mentioned limit value. Preferably, a concentration of from 90 to 160 µmol/l copper in the surrounding body fluid is intended. According to one embodiment, provision is made that the coating is single-layer. This results in low production expense.

Alternatively, provision is made that the coating is multi-layer. This allows different requirements on the implant to be satisfied by applying different layers within the coating.

It is in particular possible by means of different layers within the coating to control the rate of release of the copper ions to the surroundings. For example, a first layer of the multilayer coating may contain the copper content, and a retardation layer of TiN may be applied over this layer, which has layer properties that influence the rate of release of the copper ions on the layer surface.

Preferably, the complete antibacterial coating is provided in a thickness of from 1 to 7 µm. A thickness of from 2 to 4 µm is particularly preferred. It has been found that the desired antibacterial activity can be obtained even with such a thin coating.

The object mentioned above is also achieved by means of a method of producing an antibacterial coating of an implant, the coating containing a copper content. The special advantage of the method according to the invention resides in that a well-proven method can be used without any additional method steps to generate a coating which has the desired antibacterial properties.

For producing the coating, a PVD process is suited in particular, since in this way a very high hardness of the coating is obtained.

Provision is preferably made that the pressure of the process gas is less than 5.00E-2 mbar. With these process parameters the advantage is obtained that layers having high adhesion and high hardness can be produced.

According to a variant embodiment, provision is made that inert gases (argon, krypton) are used as process gas, and/or the reactive gases of nitrogen, oxygen and/or a hydrocarbon gas are used. This results in the advantage that layers of different hardnesses, different temperature resistances and different tribological properties can be generated.

The invention will be described below on the basis of an embodiment with reference to the accompanying Figures.

DETAILED DESCRIPTION OF THE PREFERRED EMBODIMENTS

Figure 1:
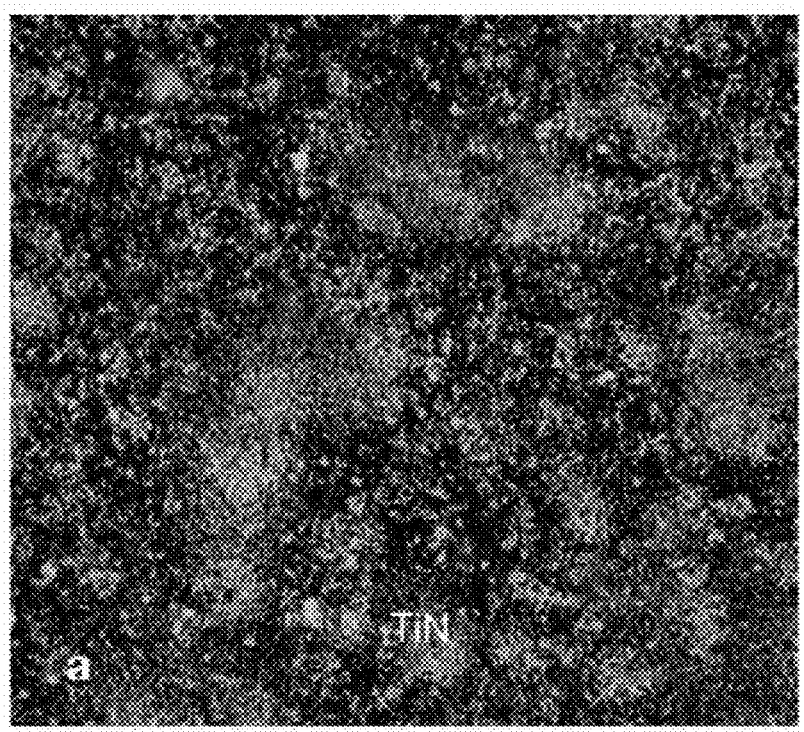
FIGS. 1 and 2 show the surfaces of different samples which were exposed to the same conditions.

It is basically applicable that the antibacterial coating of the implant according to the invention is implemented as a thin, metallic and/or ceramic layer on one or more surfaces of the implant. This layer contains the atoms of at least two metals, one of which is always the antibacterially active copper. In addition, at least one further metal, but also any desired combinations of the following metals may be included: Ti, Zr, Nb, Ta, Cr, Mo, W, Si, Al. Furthermore, the layers according to the invention may contain ceramic compounds including nitrogen, oxygen and carbon. The layers according to the invention may be employed wherever PVD layers of the above-mentioned metals and ceramic compounds are already used today and an antibacterial activity of the layer is additionally desirable.

For producing the coating, PVD processes are made use of as are basically known for the deposition of layers having high hardnesses. Depending on the requirements, the following vacuum-based coating processes may be used: arc evaporation, thermal evaporation, hollow cathode evaporation, sputtering, and ion plating. The respective requirements also determine whether mixed targets and/or pure targets are used.

An exemplary method of coating implants with the antibacterial coating will now be described below. The implants are provided with a coating consisting of a multilayer system of TiN and Cu in a plurality of underlayers. The proportion of copper in the coating is sufficiently high so as to develop an antibacterial activity. At the same time, the concentration of the copper ions released in the body is not so high as to lead to a cell-damaging effect and therefore to an impairment of the growing-on of the implant. More particularly, a copper concentration in excess of 200 µmol/l of body fluid is to be avoided.

The antibacterial activity of the exemplary coating was demonstrated by means of various titanium samples which are provided with a multilayer coating. The coating was deposited using a PVD process and was formed of titanium and copper. Nitrogen was supplied as a reactive gas here. A coating of this type is suitable in particular as a hard coating for implants.

The titanium samples were washed with an aqueous wash solution in an ultrasonic bath, then rinsed with distilled water, and subsequently dried in a drying cabinet.

After drying, the samples were placed on a rotary table in the vacuum chamber of the PVD system. The rotary table brings about a biaxial rotation of the titanium samples. In this way, a homogeneous coating in the directed beam of the coating sources can be ensured.

The PVD system that was used featured two sources, namely, an arc evaporation source and a magnetron sputtering source. A titanium target was situated in the arc evaporation source, while a copper target was used in the magnetron sputtering source.

By evacuating the chamber, the operating pressure of less than 0.025 mbar was produced. No reactive gas was used for the first operating steps.

Subsequently, the surfaces of the titanium samples were cleaned and activated in two operating steps. First the samples were baked at 300° C. for 45 min. Then, the samples were sputtered with titanium ions from the arc source at a bias voltage of −900 V for 2 min.

In a further operating step, a titanium adhesion layer was applied at a bias voltage of the samples of −150 V and an evaporation current of 70 A for 3 min., likewise using the arc source. Both values were used for the arc source in the following steps as well.

During the next operating steps, nitrogen as the reactive gas was introduced into the vacuum chamber at a defined rate.

To form the next layer, titanium nitride (TiN) was deposited onto the samples by the arc source for 10 min.

Then, the layer according to the invention is generated in the form of a multilayer sandwich layer. Starting with copper from the magnetron sputtering source (500 W power), alternating with titanium from the arc source, 24 layers were generated in this manner, 12 copper layers and 12 titanium nitride layers, respectively. The last layer is titanium nitride (TiN). The coating time was 2 min. each for each of the titanium nitride layers and copper layers.

Thereafter, the layer thickness was measured, and the elemental composition was determined using an EDX analysis (energy-dispersive X-ray spectroscopy).

The overall layer thickness of the samples amounts to 2.13 µm on an average, and the copper concentration amounts to 3.3 µg/mm$^2$ on an average.

Following this, the release of copper from the surface was examined. To this end, in order to approximate the conditions in the body as closely as possible, coated samples were placed in PBS buffer and cell culture medium at 37° C., and the amount of copper released was measured at predefined time intervals. To determine the copper content in the solutions, use was made of the photometric determination and the atomic absorption spectroscopy (AAS).

The cumulative copper concentration measured here is apparent from Table 1 below:

| days | 0 | 1 | 2 | 3 | 4 | 5 | 6 | 7 | 8 | 9 | 10 |
|---|---|---|---|---|---|---|---|---|---|---|---|
| mg/l | 0 | 13.5 | 15.4 | 16.8 | 26.2 | 28.7 | 32.1 | 32.5 | 32.9 | 33.3 | 34.4 |

The analysis of the bacterial activity was carried out using bacterial cultures in PBS buffer and in cell culture medium. All samples and sample containers were sterilized in an autoclave prior to inoculation with bacteria. All of the following processes were performed under sterile conditions. All bacterial tests were carried out using *Staphylococcus aureus* ATCC 25923 (available from the company of DOENITZ-PROLAB).

Since microorganisms living in biofilms are known to differ significantly from planktonic bacteria, both types were examined. Especially the formation of a biofilm on an implant surface is undesirable. The activity of the layer according to the invention was analyzed for both types. To this end, the samples with a predefined quantity of bacteria (1.00E+07 CFU/ml) were placed in the supernatant solution at 37° C., and the number of bacteria was determined at fixed times, for the planktonic bacteria in the solution and for the biofilm-forming bacteria on the substrate surface.

The values measured here are apparent from Table 2 below:

|  | TiCuN | TiN | PC PBS |
|---|---|---|---|
| 0 h | 9.60E+06 | 9.60E+06 | 9.60E+06 |
| 2 h | 3.50E+04 | 4.10E+05 | 3.07E+05 |
| 4 h | 1.32E+03 | 2.03E+06 | 1.98E+06 |
| 6 h | 6.90E+02 | 1.34E+07 | 6.30E+06 |
| 8 h | 6.00E+03 | 4.55E+06 | 1.29E+06 |
| 24 h | 5.00E+01 | 2.49E+06 | 7.13E+06 |

It can be seen that a highly antibacterial activity is present even though in the samples the copper layer is not exposed on the surface of the sample, but is covered by the last layer of titanium nitride (TiN).

In practice, typically fewer layers are used for coating the implant than is the case with the sample described. What is essential is that by the appropriate realization of the copper-containing layers (specifically with regard to thickness and copper content) in combination with the final layer, the release rate and release duration can be set to advantageous values. The final layer may consist of TiN, TiO, TiC or only of Ti here, depending on the requirements. In addition, Ta or Nb may be added, or else only Ta or Nb may be used.

Figure 2:
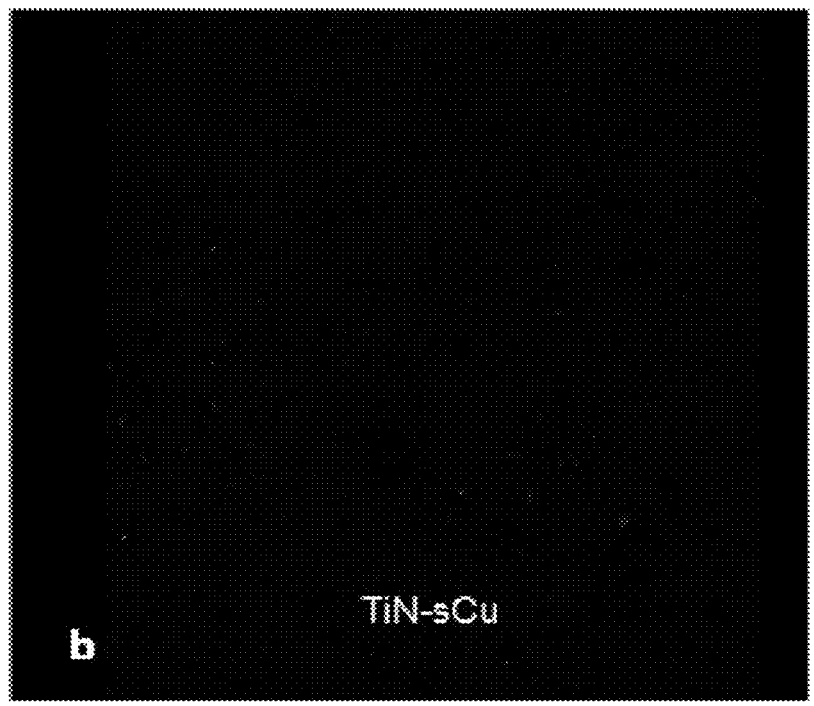

As an alternative to a coating which consists of a plurality of alternating layers of copper and titanium nitride, it is also possible to apply a single-layer coating which consists of TiCuN. A highly antibacterial activity can be obtained in this manner as well, as is shown by the comparison of FIGS. 1 and 2. FIGS. 1 and 2 show the surfaces of samples which were exposed to the same conditions. The sample in FIG. 1 is a sample of titanium nitride. The colonization by Staphylococcus aureus is clearly visible. FIG. 2 shows a sample coated with titanium nitride and copper. The surface is almost germ-free.

A single-layer coating may be produced using a mixed target which consists of a copper alloy including one or more of the metals of Ti, Zr, Nb, Ta, Cr, Mo, W, Si, Al. The advantage of this method is the reduced production expenditure. But on the other hand, there are certain restrictions in the control of the release rate of the copper.

The invention claimed is:

1. An implant coated with a coating, wherein the coating comprises at least one antibacterial coating; the antibacterial coating contains at least one layer of copper titanium nitride and is homogenous, said antibacterial coating is established by incorporating copper atoms into a titanium nitride coating, and copper is released from the antibacterial coating when implanted, such that a copper concentration of from 90 to 160 µmol/l is obtained in a body fluid surrounding the implant.

2. The coating according to claim 1, characterized in that the coating contains at least one of the following components: Zr, Nb, Ta, Cr, Mo, W, Si, Al.

3. The coating according to claim 2, characterized in that the coating contains biocompatible metals Ta and Nb.

4. The coating according to claim 1, characterized in that the coating further comprises a coating component which is bound in the form of nitrides, carbides, or oxides.

5. The coating according to claim 1, characterized in that the coating consists of one single layer.

6. The coating according to claim 1, characterized in that the coating consists of a plurality of layers.

7. The coating according to claim 6, characterized in that a plurality of layers are provided which have different structures.

8. The coating according to claim 7, characterized in that one or more layers of the multilayer coating contain the copper content, and applied over these layers are one or more retardation layers which do not contain a copper content.

9. The coating according to claim 1, characterized in that the coating is provided in a thickness of from 1 µm to 7 µm.

10. The coating according to claim 9, characterized in that the coating is provided in a thickness of from 2 µm to 4 µm.

11. The coating according to claim 1, characterized in that the implant consists of titanium or a titanium alloy.

12. The coating according to claim 1, characterized in that the coating is a PVD coating.

* * * * *